United States Patent [19]

Wolf

[11] Patent Number: 4,543,064
[45] Date of Patent: Sep. 24, 1985

[54] DENTAL BRIDGE

[76] Inventor: Ehrenfried G. B. Wolf, Rte. 1, Box 143 A, Raymond, Wash. 98577

[21] Appl. No.: 139,788

[22] Filed: Apr. 14, 1980

[51] Int. Cl.[4] ............................................. A61C 13/08
[52] U.S. Cl. .................................. 433/208; 433/211; 432/258
[58] Field of Search ............... 433/208, 209, 210, 211, 433/213, 26, 191, 196, 205, 49; 206/83; 432/258, 259; 264/17, 19; 249/54; 269/46; 164/DIG. 4

[56] References Cited

U.S. PATENT DOCUMENTS

| 548,106 | 10/1895 | Wienand | 433/209 |
| 884,977 | 4/1908 | Boos | 433/210 |
| 1,263,311 | 4/1918 | Curry | 433/208 |
| 1,503,313 | 7/1924 | Floyd | 433/208 |
| 1,696,422 | 12/1928 | Thayer | 433/211 |
| 1,875,999 | 5/1932 | Charen | 206/83 |
| 2,243,583 | 5/1941 | Stein | 206/83 |
| 2,276,701 | 3/1942 | Pusey, Jr. | 206/83 |
| 3,716,418 | 2/1973 | Kochavi | 164/DIG. 4 |
| 3,951,587 | 4/1976 | Alliegro et al. | 432/258 |
| 4,153,164 | 5/1979 | Hofmeister et al. | 432/258 |

FOREIGN PATENT DOCUMENTS

| 606551 | 6/1926 | France | 433/208 |
| 433980 | 4/1948 | Italy | 433/209 |
| 63898 | 10/1912 | Sweden | 433/210 |
| 411451 | 6/1934 | United Kingdom | 433/209 |

*Primary Examiner*—John J. Wilson

[57] ABSTRACT

This invention is directed to the use of a false tooth having an attaching means rearwardly directed on the rear of the false tooth. The attaching means makes it possible to more definitely and more easily position the false tooth while working an individual tooth and while forming the dental bridge.

After the dental bridge has been formed the attaching means can be removed so as to have the finished dental bridge.

The result is that a desirable dental bridge can be prepared from factory made false teeth and also can be prepared in less time and with less expense than the conventional method prior to this invention.

5 Claims, 17 Drawing Figures

FIG. 1
FIG. 4
FIG. 3
FIG. 2
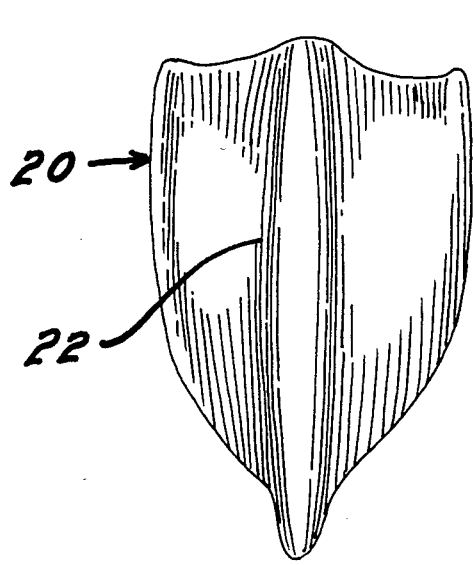
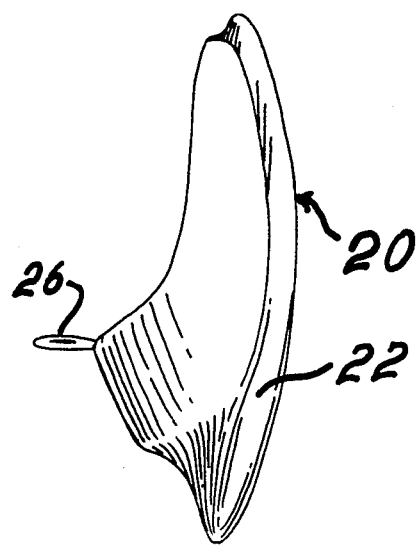
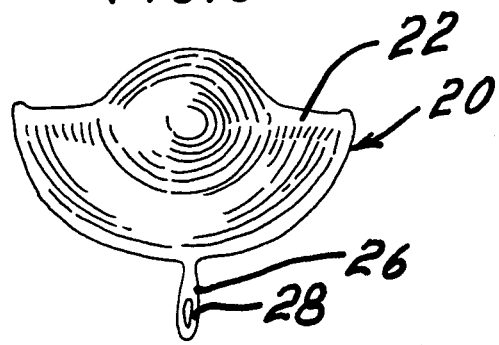
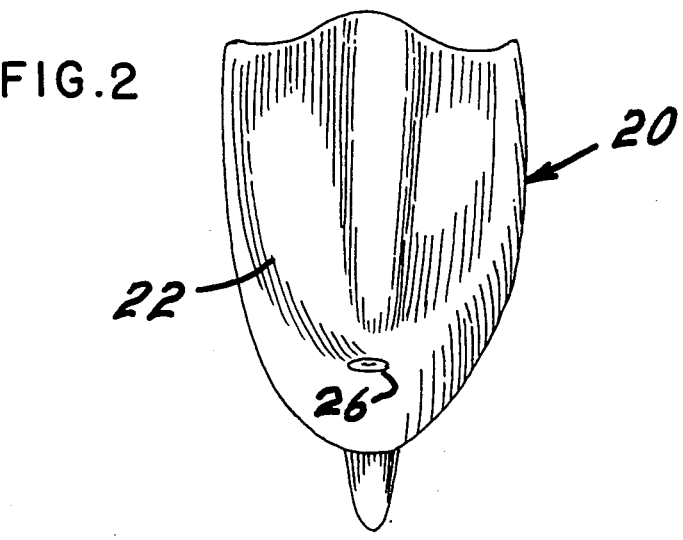

DENTAL BRIDGE

A BRIEF SUMMARY OF THE INVENTION

This invention is for a dental bridge wherein there can be used a factory prepared false tooth or a false tooth that is mass produced.

The false tooth comprises a metal base having a porcelain overlay.

On the rear of the metal base there is an attaching means such as a loop or a pin. The purpose of the loop or the pin is to make it possible to more easily and more definitely position the tooth while making the dental bridge.

A dental bridge is prepared from individual false teeth. At times, prior to this invention, it was difficult to position the individual false teeth while making the dental bridge. Further, after the dental bridge had been made a dental technician would grind and finish the false teeth to a desired configuration and a desired size. The working of false teeth in a bridge is more difficult than the working of an individual false tooth. In fact, false teeth in a dental bridge cannot be worked to give a natural appearance. The outer edges of the teeth are abraded away. The result is a V-appearance between adjacent teeth. A V-appearance between adjacent teeth is not a natural appearance. With this invention a dental technician can grind and work each false tooth individually before placing in the dental bridge. The result is a more natural appearance of the false teeth in the bridge.

After the dental bridge has been prepared the rearwardly directed attaching means or metal loop or metal pin can be removed.

THE DRAWINGS

FIG. 1 is a labual view, a front view, of a metal base for a false tooth without a porcelain overlay;

FIG. 2 is a lingual view, a rear view, of a metal base for a false tooth without the porcelain overlay and show the metal base and the metal loop attaching means at the rear of the metal base;

FIG. 3 is a labial view, a top plan view, of a metal base for a false tooth without the porcelain overlay and shows the metal base and the metal loop at the rear of the metal base;

FIG. 4 is a mesial view, a side view, of a metal base for a false tooth without the porcelain overlay and shows the metal base and the metal loop at the rear of the metal base;

Figure 16:
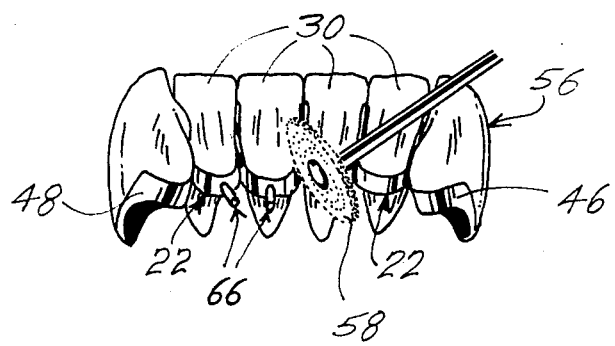
Figure 17:
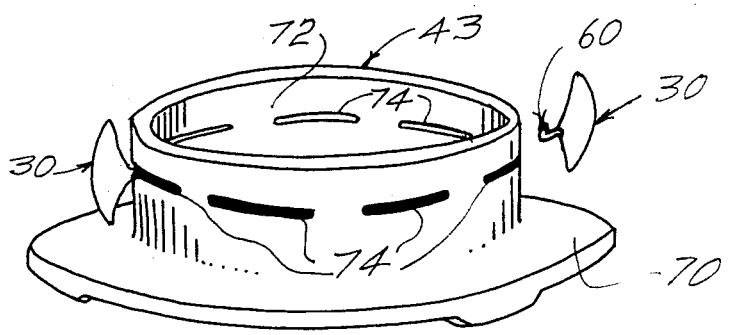

FIG. 16 is a rear elevational view showing removal of the attaching means from the metal base of the false teeth after the dental bridge has been formed; then, FIG. 17 is a positioning stand for positioning individual false teeth in the process for making a dental bridge, and which positioning stand is of ceramic and makes it possible to work on an individual tooth and then, if necessary, heat treat the tooth in a furnace.

THE DETAILED DESCRIPTION OF THE INVENTION

This invention is directed to the making of a dental bridge from a new type of false tooth. The new type of false tooth has an attaching means on the rear of the tooth to make it possible to position the tooth while working on an individual tooth and, also, while preparing the dental bridge. This attaching means makes it possible to more quickly, to more positively, and to more inexpensively make the dental bridge as less time is required to make the dental bridge.

In FIGS. 1 through 4 there is illustrated a basic tooth 20 having a metal base 22. The metal base is the supporting structure for a porcelain overlay. It is seen that on the rear of the metal base 22 that there is an attaching means 26.

The attaching means 26 comprises an outwardly directed finger or protrusion, substantially flat, having a hole or passageway 28.

The basic tooth 20 does not have the porcelain overlay. The porcelain overlay is for decorative purposes or cosmetic purposes as well as for the useful purpose of biting, chewing and grinding.

In FIGS. 5 through 8 there is illustrated the false tooth 30 having the porcelain overlay 32. It is to be understood that the porcelain overlay 32 is positioned over the metal base 22 of the basic tooth 20.

Figure 11:
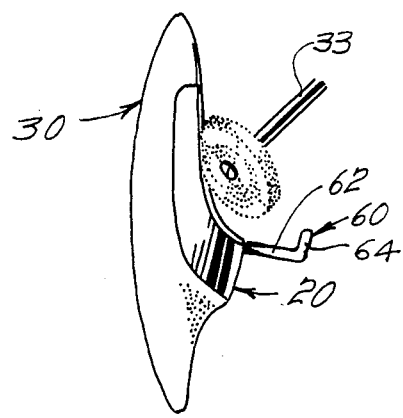
FIG. 11 is a mesial view of a false tooth comprising a metal base with the porcelain overlay and illustrates the metal loop at the rear of the tooth and also illustrates a polishing and grinding means for working with teeth and, in particular, illustrates a brush for working the metal base.

In FIG. 11 there is illustrated the false tooth 30. The metal base 22 of the basic tooth 20 is being worked and finished by a rotating brush 33.

The basic tooth 20 can be ordered from the factory. Then, it can be worked and finished to the desired size so as to accept the porcelain overlay 32.

Figure 12:
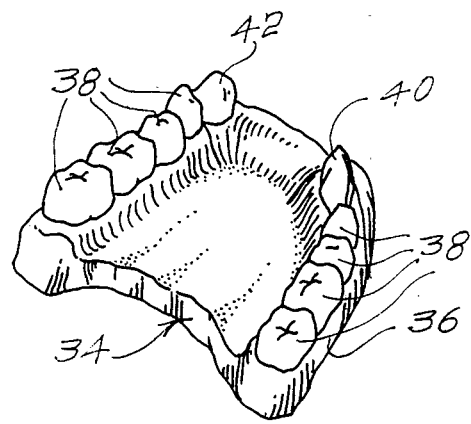
FIG. 12 is a rear perspective view looking at the teeth in a model and with the four front teeth missing thereby indicating the need of a bridge and illustrates crowns on the two stub teeth of FIG. 10.

In FIG. 12 there is a fragmentary view of a model of a lower jaw 34 of an individual. The lower jaw 34, naturally, comprises simulated gums 36. In the model there are also simulated natural teeth 38. In FIG. 12 it is seen that there are four simulated natural teeth 38 on each side of the jaw.

Figure 10:
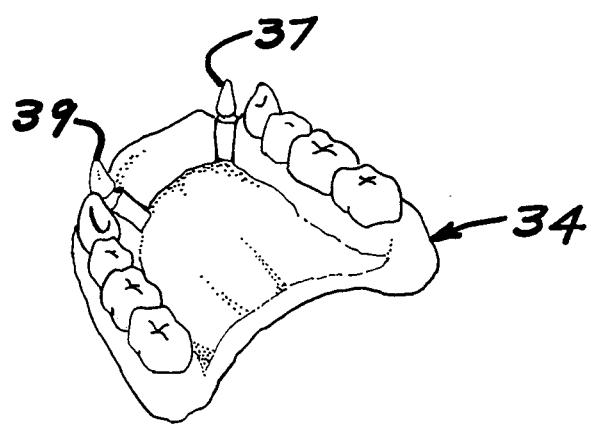
FIG. 10 is a perspective view of a model for a lower jaw and shows a vacant place for four teeth and a stub of a tooth on each side of the vacan place for four teeth.

In FIG. 10 the model of the lower jaw illustrates a vacant place 35 at the front of the jaw. The vacant place can receive four false front teeth. On each side of the vacant place there are stub teeth 37 and 39. The stub tooth has been worked or processed to receive a crown. The crowns on the stub teeth 37 and 39 are referred to as crowns 40 and 42. In other words, in FIG. 10 there is illustrated a mode of a jaw 34 having four simulated natural teeth on each side of the jaw. The four front lower teeth are missing. It is desired to make a dental bridge having the four front teeth replaced with four false teeth. To secure and position the dental bridge there is used the two crowned teeth having crowns 40 and 42 on the stub teeth 37 and 39.

To assist in the preparation of the dental bridge there is used a positioning stand 43, see FIG. 17. The use of the positioning stand 43 will be more fully explained the a latter part of the specification.

Figure 13:
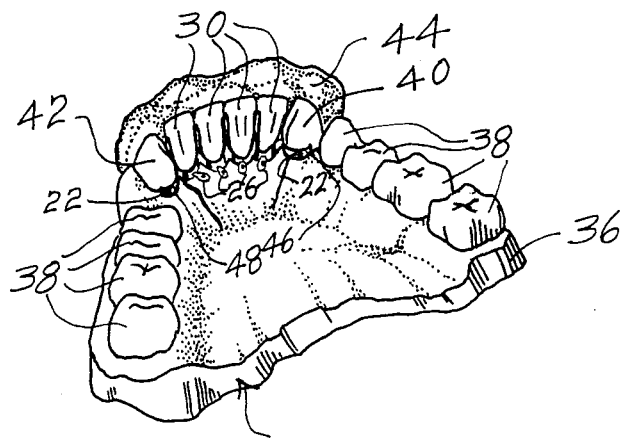
FIG. 13 is a rear perspective view of a dental bridge of six false teeth in a model of a lower jaw and with the six false teeth held in position by a plaster matrix with the plaster matrix being on the front of the teeth, and illustrates the metal loops on the rear of the teeth.

In preparing the dental bridge a plaster matrix 44 is formed around the front of the four false teeth 30 and the two crowns 40 and 42, see FIG. 13. In FIG. 13 it is seen that the four front false teeth 30 have an attaching means 26 projecting rearwardly from each of the teeth. Also, there is a brace 46 connecting with the outside right front false tooth. This brace 46 is adapted to fit with the crown 40. Further, there is a brace 48 connecting with the outside left front false tooth 30. The brace 48 is adapted to fit with the crown 42.

Again, the plaster matrix 44 is used to assist in positioning the four false teeth 30 and the two crowns 40 and 42 prior to soldering the metal base 22 of each false tooth 30 to the adjacent metal base 22 of the adjacent false tooth. The plaster matrix 44 makes it possible to hold the four front false teeth 30 and the two crowns 40 and 42.

If the spacing or the appearance of the false teeth 30 in the dental bridge does not appear to be correct the teeth can be removed from the plaster matrix 44 and reworked and finished as individual teeth, see FIG. 11 for illustrative purposes.

Figure 14:
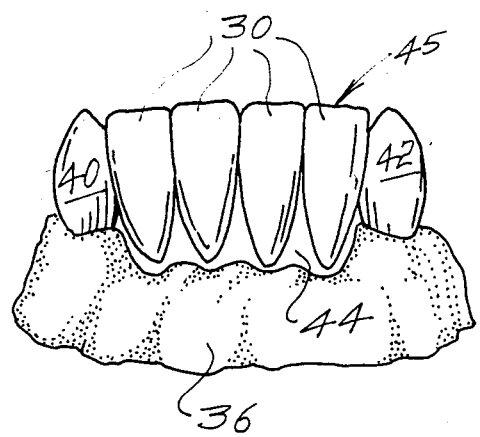
FIG. 14 is a front elevational view of the six false teeth in the dental bridge and illustrates a crowned tooth on each side of the four false teeth in the dental bridge.

In FIG. 14 there is illustrated, a front view of the four front false teeth 30 and the two crowns 40 and 42 in the plaster matrix 44 after the major part of the matrix has been removed. It is seen that the lower part of the teeth 30 are still in the plaster matrix 44.

The four front false teeth 30 and the two crowns 40 and 42 are in the formative dental bridge 45, see FIG. 14.

Figure 15:
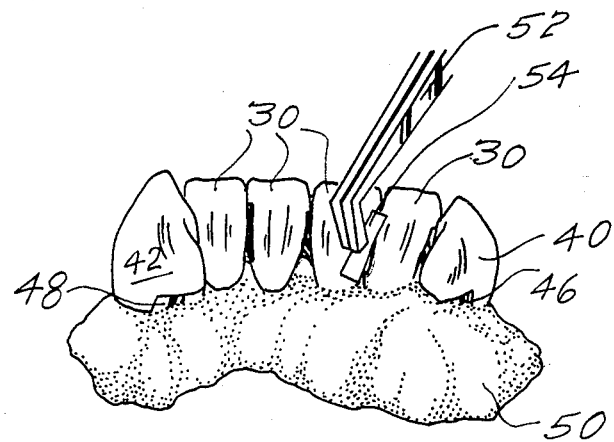
FIG. 15 is a rear elevational view of the six false teeth held in a solder investment and also illustrates tweezers holding solder so as to further solder together the metal base of adjacent false teeth.

Then, the porcelain overlay of the teeth 30 and the crowns 40 and 42 is covered with a protective agent such as wax. After the porcelain overlay has been covered with the wax the rear of the teeth 30 and the crowns 40 and 42 in the formative dental bridge 45 can be placed in a solder investment 50, see FIG. 15. In FIG. 15 there is illustrated a rear view of the four front false teeth 30 and the crowns 40 and 42 in the formative dental bridge 45 and the lower part of the teeth 30 and the crowns, and that part having the metal base 22 exposed, are in the solder investment 30. Then, a dental technician with tweezers 52 and a strip of solder 54 can solder together metal base 22 of adjacent teeth 30 and the crowns 40 and 42. In this manner the adjacent front false teeth 30 and the crowns 40 and 42 are formed into a dental bridge.

The purpose of the protective coating or the wax on the porcelain overlay of the false teeth 30 and the crowns 40 and 42 is to prevent the damaging of the porcelain overlay and also the adherance of the solder, in the solder investment 50, to the porcelain overlay. After the adjacent false teeth 30 and the crowns 40 and 42 have been united by solder 54 and also the lower part of the false teeth 30 and the crowns 40 and 42 have been united by the solder investment 50 the excess solder investment 50 is removed. This leaves a dental bridge 56, see FIG. 16. In FIG. 16 there is illustrated the four false teeth 30 and the crowns 40 and 42 in the dental bridge 56 and there is illustrated a rotating brush 58 for removing the attaching means 26 on the back of the metal base 22 of the false teeth. After the attaching means 26 has been removed the false teeth 30 and the dental bridge 56 is ready to be worn by the person for whom it was made.

Figure 9:
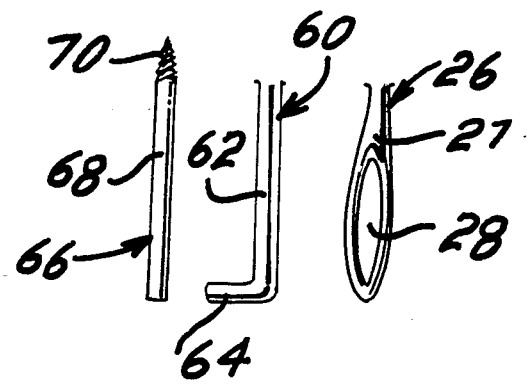
FIG. 9 illustrates three different attaching means for connecting with the metal base wherein 9-A illustrates a pin for screwing into the metal base for temporarily positioning the false tooth; 9-B illustrates a pin which is unitary or integral with the metal base of the false tooth; and, 9-C illustrates a loop which is unitary or integral with the metal base of the false tooth.

In FIG. 9 there is illustrated a number of attaching means.

FIG. 9-C shows the attaching means 26 comprising a rearwardly projecting part 27 having a passageway 28. The attaching means 26 is unitary or integral with the metal base 22. The attaching means 26 is cast with the casting of the metal base 22.

FIG. 9-B illustrates a pin 60 having a main body 62 and on the outer end having an angled member 64. As is seen in FIG. 9-B the angled member 64 is, substantially, right angles to the main body 64. The attaching means 60 or the pin 60 is unitary or integral with the metal base 22. The attaching means 60 is cast with the casting of the metal base 22.

FIG. 9-C illustrates an attaching means 66 or a pin 66 having a main body portion or a shank portion 68 and a threaded tapered end 70. The pin 66 is screwed into the metal base 22. After the dental bridge has been completed the pin 66 can be removed from the false tooth by unscrewing the pin from the metal base.

In FIGS. 2, 3, 4, 6, 7 and 13 there is illustrated an attaching means 26 on the metal base 22.

Figure 6:
FIG. 6 is a lingual view, a rear view, of a false tooth with the porcelain overlay on the metal base and illustrates the metal loop at the rear of the false tooth.
Figure 7:
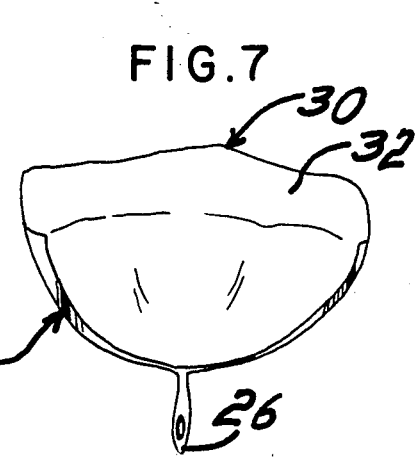
FIG. 7 is a labial view, a top plan view, of a false tooth with the porcelain overlay on the metal base and illustrates the metal loop at the rear of the false tooth.

In FIGS. 6, 16 and 17 there is illustrated the attaching means 60 on the metal base 22.

Figure 5:
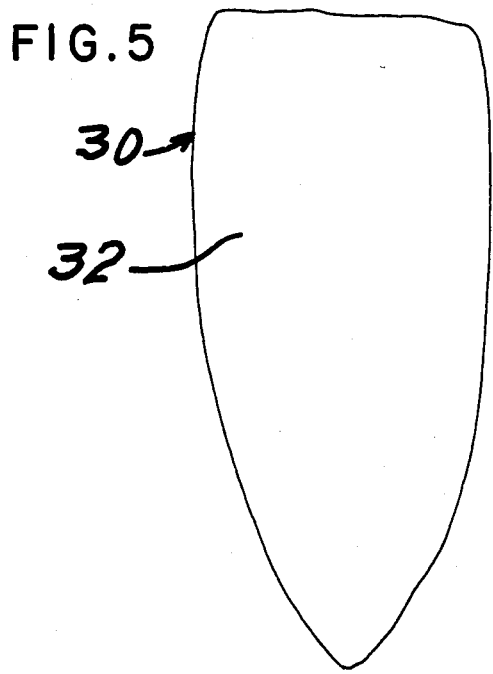
FIG. 5 is a labual view, a front view, of a false tooth with the porcelain overlay on the metal base.
Figure 8:
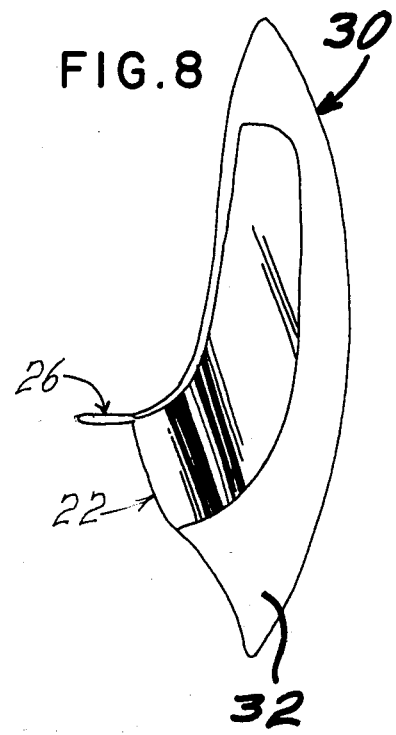
FIG. 8 is a mesial view, a side view, of a false tooth with the porcelain overlay on the metal base and illustrates the metal loop at the rear of the false tooth.

In FIGS. 8, 11 and 16 there is illustrated the attaching means 66 in the metal base 22.

Now, with reference to the positioning stand 43 in FIG. 17 it is seen that there is a base 70 integral or unitary with a support 72. The support 72 may be considered to be a wall. In the wall there is a series of horizontal or circular slots 74.

In using the positioning stand 43 the false tooth or teeth 30 can be so positioned that the attaching means 26 or 60 or 66 is placed in a slot 74. The slot may be of such a length that two or more false teeth 30 can be positioned in the slot 74. With a false tooth 30 positioned in the slot it is possible to abrade away or to grind away the excess tooth or excess porcelain. Also, it is possible to individually work or to process each tooth so as to have a finished false tooth which appears to be a natural tooth. If it be necessary to alter or to repair the procelain on the false tooth this can be accomplished. Then the false teeth can be placed in a furnace and heat treated.

The positioning stand 43 serves the purpose of positioning a false tooth while the dental technician is working or processing the false tooth. The positioning stand 43 assists in firmly positioning the false tooth while the dental technician is working the false tooth. The positioning stand 43 saves the time of the dental technician and thereby saves money for the person having a dental bridge made.

The positioning stand 43 is made of ceramic so that it can be placed in a furnace to fire the porcelain of a false tooth.

The dental bridge has been described as having six teeth of which there are four false teeth for the four missing front teeth in the lower jaw of an individual, and two crowns 40 and 42 for the stub teeth 37 and 39.

It is to be realized that the dental bridge may comprise three false teeth or may comprise more than three false teeth or more than four false teeth. Also, the position of the dental bridge is not restricted to the four front teeth of an individual but can be the other teeth of the individual or can be a combination of the front teeth of an individual and the side teeth of the individual. The type of dental bridge and the requirements of the dental bridge will vary from individual to individual.

My invention can be used for anterior teeth and posterior teeth.

The invention, in my opinion, has some advantages in that the basic tooth 20 comprising the metal base 22 can be manufactured in a factory in large number and does not need to be manufactured by a dental technician. A result of this is that I consider that the resulting false tooth 30 will be less expensive than a false tooth prepared by present dental technicians. In addition, a less skilled dental technician can be used for preparing the dental bridge as the less skilled dental technician need not know how to make a false tooth 30. The false tooth 30 is a factory product.

A further advantage in my opinion is that the dental technician can work and modify an individual tooth to a desired configuration and to a desired cosmetic effect. If a false tooth is in a dental bridge it is more difficult to work the false tooth as compared with a false tooth separate and apart from a dental bridge. A false tooth separate and apart from a dental bridge is easier to work and to modify to achieve a desired cosmetic effect. It is not possible to modify a false tooth in a bridge to have as pleasing aesthetic effect as an individual false tooth which has been worked individually.

With the basic tooth 20 prepared at a factory and also the false tooth 30, substantially, prepared at a factory there is a saving in time in preparing the teeth, as compared with conventional methods used prior to the introduction of this invention, and therefore a saving in cost of the finished tooth. Also, there is a saving in electricity and energy as there are fewer firings of the teeth to make the solder investment 50 of the formative dental bridge 45.

In addition, I consider that it is possible to reduce the number of sizes for the base of the tooth 20 so as to probably have only one or two major sizes for the base of the tooth 20.

Another value of this invention is that it is possible with the loop or the pin to have a fastening means for the base of the tooth while the tooth is being positioned and connected into the bridge. Prior to this invention it has been a time consuming and frustrating operation to try and position the tooth while making the dental bridge.

In the preparation of this patent application a patent search was made and the following interesting patents were found:

J. E. Johnson: U.S. Pat. No. 1,670,361;

Yirikian: U.S. Pat. No. 1,841,870;

Weissman: U.S. Pat. No. 3,348,311.

I consider that my invention defines over each of these respective patenties. For example, Johnson teaches of a tooth band. My invention is directed to a false tooth having an attaching means rearwardly directed for ease in making a dental bridge. The subject matter of my invention and that of Johnson are dissimiliar.

With respect to Yirikian it is noted that he teaches of a arch spring vertically split removable dental bridge work. He does not teach of a false tooth having a rearwardly directed attaching means. I consider that the teaching of the Yirikian to be entirely dissimiliar from my invention.

Weissman teaches of the use of a splint for supporting and more definitely positioning the teeth positioning the teeth in the mouth. Again, I consider that the teaching of Weissman is not the same as the teaching of my invention Weissman is the teaching of a brace for supporting teeth. My invention is the teaching of a false tooth having a rearwardly directing attaching means for use in making a dental bridge.

I consider my invention to be new as I know of no other false tooth having rearwardly directing attaching means for use in the making of a dental bridge and which attaching means is useful in the initial positioning of the false tooth in a formative dental bridge. Also, I consider my invention to be unobvious as I have not heard and have not seen of another false tooth having a rearwardly directed attaching means for use in initially positioning the false tooth in the making of a dental bridge. The patent search did not disclose a similar teaching.

With a dental bridge of six teeth I figure that the bridge, using my invetion and teaching, can be made in less than one-half of the time required by prior conventional methods. Naturally, there is a saving of money and costs. With a dental bridge of three teeth I figure that the bridge can be made in about three-quarters of the time required by prior conventional methods.

RESUME

From the foregoing it is seen that I have disclosed a basic tooth 20 having a metal base 22 and a supportive structure 24.

On the rear of the metal base 22, and rearwardly directed, there is an attaching means 26. Further, there is a porcelain overlay 32 for the basic tooth 20.

In the formation of a dental bridge there is used a positioning stand 43. The false tooth 30 can be positioned in the positioning stand with the attaching means 26 in an appropriate slot 74 so that the tooth can be individually worked or processed.

Then, a plaster matrix 44 can be formed around the front of the false teeth 30. After the false teeth 30 and the plaster matrix 44 have been formed changes can be made with respect to the size and configuration and cosmetic effect of the false teeth 30, if necessary.

After the teeth have been adjusted in the plaster matrix 44 there can be a solder investment 50 around the rear of the false teeth 30 with the solder investment contacting the metal base 22 of the false teeth. Then, with the false teeth 30 definitely positioned in the solder matrix 50 in the upper part of the false teeth and that part of the metal base 22 can be soldered to the adjacent individual teeth so as to form the dental bridge 44.

The solder investment can be removed. Then, the attaching means on the rear of the teeth and dental bridge can be removed. By this time the attaching means have served the desired purpose and are superflous.

I consider my invention is new as I have never seen or heard such a metal base in combination with an attaching means to assist in making a false tooth.

My invention is useful in that it is possible to make a false tooth having a pleasant cosmetic effect, and to make a dental bridge is less time than by prior conventional methods.

My invention is unobvious in that I known of no similar invention or of no similar teaching.

From the foregoing and having presented my invention what I claim is:

1. A combination of a false tooth and a positioning stand:
   a. said false tooth comprising:
      I. a metal base;
      II. an overlay overlying most of said metal base to simulate a natural tooth;
      III. an attaching means connecting with the rear of said metal base;
   b. said positioning stand comprising:
      I. a support;
      II. a slot in said support;
      III. said slot being capable of receiving and positioning an attaching means connecting with the rear of a metal base for a false tooth;
   c. wherein said attaching means is positioned in said slot to position said tooth; and, d. Said support being capable of being heated to a temperature sufficiently high to fuse a porcelain overlay to said metal base to make a false tooth.

2. A process for making a dental bridge, said process comprising:
   a. preparing a plurality of false teeth having a metal base and an attaching means connecting with the rear of the metal base;
   b. working, if necessary, said false tooth to the desired configuration;
   c. forming a solder matrix to include said attaching means and to position said teeth;
   d. uniting the metal base of the teeth;
   e. removing the excess solder matrix;
   f. removing the attaching means.

3. A process for making a dental bridge, according to claim 2 and comprising:
   a. after working said false teeth to the desired configuration placing a positioning means on the front of the teeth; and,
   b. forming said solder matrix on the rear of the teeth.

4. A process for making a dental bridge, according to claim 3 and comprising:
   a. said positioning means on the front of the false teeth being a plaster matrix; and,
   b. soldering the metal base of the teeth to unite the metal base of the teeth.

5. A process for making a dental bridge, according to claim 4 and comprising:
   a. prior to placing the positioning means on the front of the false teeth positioning the teeth in the desired pattern so as to be able to receive said plaster matrix; and,
   b. then positioning said plaster matrix on the front of said false teeth.

* * * * *